Jan. 20, 1942. R. L. BYRUM Plant Pat. 500
ROSE PLANT
Filed Sept. 10, 1941
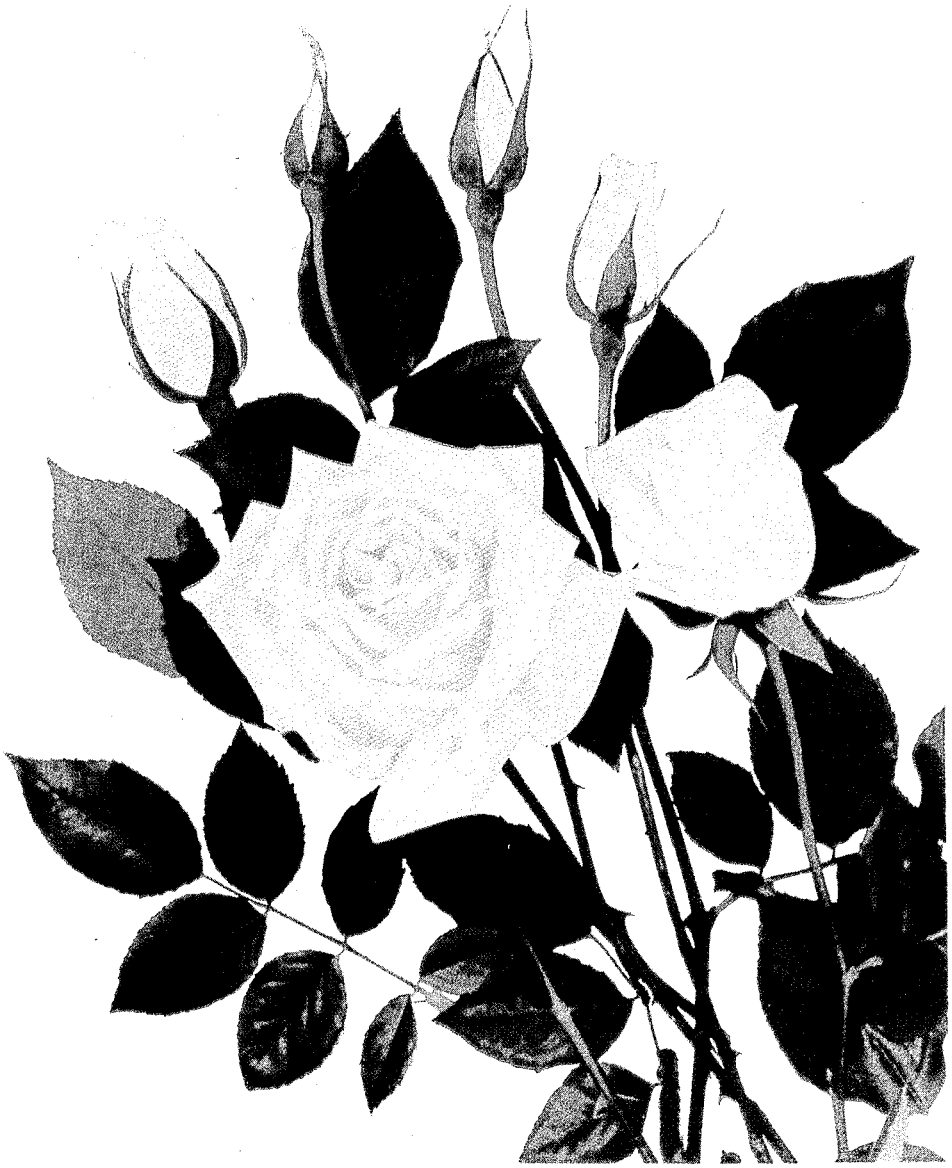
INVENTOR
R. L. Byrum
By Robb & Robb
Attorneys Patented Jan. 20, 1942

Plant Pat. 500

UNITED STATES PATENT OFFICE

500

ROSE PLANT

Roy L. Byrum, Richmond, Ind., assignor to Joseph H. Hill Company, Richmond, Ind., a corporation of Indiana Application September 10, 1941, Serial No. 410,338

1 Claim. (Cl. 47—61)

The present invention relates to a new and distinct variety of rose plant of the hybrid tea class, the result of a definite effort to obtain a rose responsive to greenhouse forcing methods designed to produce high quality and long stem cut flowers.

In carrying out this objective, I crossed the well-known greenhouse forcing variety "Joanna Hill," of the yellow color range, and "R. M. S. Queen Mary" (Plant Patent No. 249) of the pink range, thereby producing the present rose having the following primary characteristics:

(*a*) Produces long stems in greenhouse without artificial means, or from the "cut" without pinching;

(*b*) Produces long buds so desirable in cut flowers;

(*c*) Provides a good summer forcing rose as well as a winter one; and (*d*) Is resistant to mildew and blackspot.

In addition to the foregoing, its main distinguishing feature is the unusual color combination of its flowers, a color unlike that of any forcing variety of which I am aware, and illustrated as nearly correct as possible in the accompanying drawing in the various stages of development.

The color terminology herein employed is in accord with Ridgway's Color Standards where indicated by plate numbers, otherwise with general dictionary meaning.

The following is a detailed description of this new variety of rose:

Type: Greenhouse; seedling; for cut flowers.
Class: Hybrid tea.
Breeding: Seedling.
*Seed Parent.*—"Joanna Hill."
*Pollen Parent.*—"R. M. S. Queen Mary."
Propagation: Holds its distinguishing characteristics through succeeding propagations by cuttings, grafting, and budding.

*Flower*

Locality where grown: Richmond, Indiana.
Flowers borne: Singly to stem; on strong, long stems.
Quantity of bloom: Free in greenhouse.
Continuity: Continuous.
Fragrance: Slight; tea.
Bud:
*Peduncle.*—Long; slightly curved; Calliste Green, Plate VI; entirely smooth; few prickles very light in color and transparent.
*Before calyx breaks. — Size — medium. Form*—long, pointed with a conspicuous neck; with foliaceous appendages on the surface of the bud; with much cut foliaceous parts extending beyond the tip of the bud equal to three-fourths or more of its length.
*As calyx breaks.—Base*—Apricot Yellow, Plate IV, gradually changing to Jasper Red at tip, Plate XIII.
*As first petal opens.—Size*—large. *Form*—long; pointed. *Color:* outside base—Apricot Yellow, Plate IV, overlaid with Light Jasper Red toward tip, Plate XIII; inside base—Lemon Chrome, Plate IV, overlaid with Light Jasper Red toward tip, Plate XIII. *Opening*—opens up well.
Bloom:
*Size.*—When fully open—large; 4½ to 5½ inches.
*Petalage.*—Double (more petals, but the stamens not hidden); from 25 to 35 petals; arranged irregularly.
*Form.*—Full; becoming open; petals remaining at first loosely rolled outward; becoming later, at maturity, very loosely rolled outward.
Petals: Thick; with inside and outside satiny.
*Shape.*—Outside—obovate; scalloped with one notch. Intermediate—obovate; scalloped with one notch. Inside—obovate; scalloped with one notch.

This description of a newly opened flower was made from a rose grown in a greenhouse during the month of July, 1941, at Richmond, Indiana:

*Color.*—Outside petal, outside surface—Venetian Pink, Plate XIII, with Alizarine Pink edge on each edge, Plate XIII, of Lemon Chrome veins, Plate IV; inside surface—Livid Pink, Plate XXVII. Intermediate petal, outside surface—Jasper Pink, Plate XIII; inside surface—Chatenay Pink, Plate XIII. Inner petal, outside surface—Old Rose, Plate XIII; inside surface—Light Coral Red, Plate XIII, with tip edge Light Jasper Red, Plate XIII. Base in each of above instances—Lemon Chrome, Plate IV.

This description was made from a rose that was open for three days in a greenhouse in the month of August, 1941, at Richmond, Indiana:

*Color.*—Outside petal, outside surface—Rocellin Purple tip shading to Rhodonite Pink and on into Pale Rhodonite Pink, Plate XXXVIII; inside surface—Shrimp Pink, Plate I. with Livid Pink veins, Plate XXVII, Inside petal, outside surface—Rhodonite Pink shading to Pale Rhodonite Pink, Plate XXXVIII; inside surface—Shrimp Pink, Plate I, with Livid Pink veins, Plate XXVII. Base in each of above instances—Lemon Chrome, Plate IV.

*General color effect.*—Newly opened flower—Orient Pink, Plate II. Three days open—Pale Rhodonite Pink, Plate XXXVIII.

*Behavior.*—Persist.

*Flower longevity.*—As cut roses grown in greenhouse kept at living room temperatures, four days in August.

*Reproductive organs*

Stamens: Many; arranged irregularly about pistils.

Filaments: Medium length; Yellow; most with anthers.

Anthers: Medium size; Brown; all open at once.

Pollen: Very abundant; Gold.

Pistils: Medium number.

Styles: Even; medium length; medium heavy; bunched.

Stigma: White.

Ovaries: All enclosed in calyx.

Hips: Short; globular, with inconspicuous neck; rough; dull Green streaked with Rust; none ripe enough to open in August, 1941.

Sepals: Very long; permanent; curled.

*Color.*—Inside—Light Bice Green, Plate XVII; Outside—Parrot Green, Plate VI.

Seeds: No seeds available, August, 1941.

*Plant*

Foliage:

*Leaves.*—Compound of five to seven leaflets; abundant; large; heavy; leathery.

*Leaflets.*—*Shape*—ovate with acuminate apex. *Base*—acute. *Margin*—simply irregularly serrate.

*Color.*—*Mature:* upper surface—Dark Dull Yellow Green, Plate XXXII, under surface—Pois Green, Plate XLI. Young: upper surface—Forest Green, Plate XVII, entire edge Bronze; under surface—Light Bice Green, Plate XVII, overlaid with Bronze.

*Rachis.*—Medium heavy. *Upper side*—grooved; prickly. *Under side*—sparsely thorny.

*Stipules.*—Moderately long; medium width; with points turning out at an angle of less than 45°.

*Disease.*—Resistant to mildew and blackspot.

Growth:

*Habit.*—Upright.

*Growth.*—Vigorous.

*Canes.*—Heavy.

*Main stems.*—Dull Green streaked with Rust. (Old stems entirely Rust.) *Thorns*—several; medium length; hooked downward, with long, narrow base. *Prickles*—none. *Hairs*—none.

*Branches.*—Bright Green, no Rust, Calliste Green, Plate VI. *Thorns*—several; medium length; hooked downward, with long, narrow base. *Prickles*—none. *Hairs*—none.

*New shoots.*—Dull Bronze. *Thorns*—several; medium length; hooked downward, with long, narrow base. *Prickles*—none. *Hairs*—none.

I claim:

A new and distinct variety of rose plant of the hybrid tea class, characterized as to novelty, by its excellent greenhouse forcing qualities for production of cut flowers; its long stems and disease resistant foliage; and the long bud form and unusual color combination of its flowers, substantially as shown and described.

ROY L. BYRUM.